[19] United States Patent
Krapcho

[11] 4,122,255
[45] Oct. 24, 1978

[54] SUBSTITUTED AMIDES AND SULFONAMIDES CONTAINING A HETEROCYCLIC GROUP HAVING ANTIINFLAMMATORY ACTIVITY

[75] Inventor: John Krapcho, Somerset, N.J.

[73] Assignee: E. R. Squibb & Sons, Inc., Princeton, N.J.

[21] Appl. No.: 835,099

[22] Filed: Sep. 21, 1977

Related U.S. Application Data

[63] Continuation-in-part of Ser. No. 736,990, Oct. 29, 1976, Pat. No. 4,064,125.

[51] Int. Cl.² .............. C07D 207/20; C07D 211/70; C07D 295/08
[52] U.S. Cl. .................... 542/421; 544/160; 544/165; 544/177; 260/293.73; 260/293.76; 260/332.3 R; 544/400; 544/398
[58] Field of Search .............. 260/558 P, 570.7 R; 542/416, 417, 421

[56] References Cited

U.S. PATENT DOCUMENTS

| | | | |
|---|---|---|---|
| 2,774,766 | 12/1956 | Goldberg | 260/294.7 |
| 3,551,492 | 12/1970 | Mizzoni | 260/570.5 R |
| 4,064,125 | 12/1977 | Krapcho | 260/558 P X |

*Primary Examiner*—Allen B. Curtis
*Attorney, Agent, or Firm*—Lawrence S. Levinson; Merle J. Smith; Donald J. Barrack

[57] ABSTRACT

Compounds having the formula

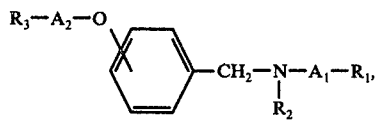

wherein $R_1$ is alkyl, cycloalkyl or aryl; $R_2$ is acyl or sulfonyl; $R_3$ is a nitrogen containing heterocyclic group; $A_1$ is a saturated bond or an alkylene group having 1 to 4 carbon atoms; and $A_2$ is an alkylene group having 2 to 5 carbon atoms; have antiinflammatory activity.

9 Claims, No Drawings

SUBSTITUTED AMIDES AND SULFONAMIDES CONTAINING A HETEROCYCLIC GROUP HAVING ANTIINFLAMMATORY ACTIVITY

This application is a continuation-in-part of copending U.S. patent application Ser. No. 736,990, filed Oct. 29, 1976, now U.S. Pat. No. 4,064,125.

BRIEF DESCRIPTION OF THE INVENTION

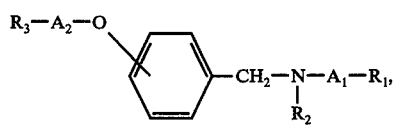

or a pharmaceutically acceptable salt thereof, have useful antiinflammatory activity. In formula I, and throughout the specification, the symbols are as defined below.

$R_1$ can be alkyl, cycloalkyl or aryl;

$R_2$ can be

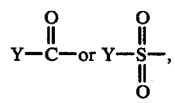

wherein Y can be alkyl, cycloalkyl, aryl, arylalkyl, styryl, or styryl wherein the phenyl group is substituted with a halogen, alkyl, alkoxy, trifluoromethyl, nitro or amino group;

$R_3$ can be alkylamino, dialkylamino or a nitrogen containing heterocyclic group selected from 1-pyrrolidinyl, 1-piperidinyl, 4-morpholinyl, 1-piperazinyl, and 4-alkyl-1-piperazinyl;

$A_1$ can be a saturated bond or an alkylene group having 1 to 4 carbon atoms; and $A_2$ can be an alkylene group having 2 to 5 carbon atoms.

The terms "alkyl" and "alkoxy," as used throughout the specification, whether by themselves or as part of larger groups, refer to groups having 1 to 6 carbon atoms.

The term "aryl", as used throughout the specification, whether by itself or as part of a larger group, refers to phenyl or phenyl substituted with a halogen, alkyl, alkoxy, trifluoromethyl, nitro, or amino group.

The term "halogen," as used throughout the specification, refers to fluorine, chlorine, bromine and iodine; chlorine and bromine are preferred.

The term "cycloalkyl," as used throughout the specification, refers to cycloalkyl groups having 3 to 7 carbon atoms.

The term "alkylene," as used throughout the specification, refers to a straight or branched chain, divalent, saturated hydrocarbon group.

DETAILED DESCRIPTION OF THE INVENTION

The compounds of this invention can be prepared using as starting materials a benzaldehyde having the formula

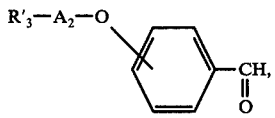

wherein $R'_3$ is alkylbenzylamino, dialkylamino or a nitrogen containing heterocyclic group, and a primary amine having the formula $$H_2N-A_1-R_1 \quad \text{III.}$$

Reaction of a benzaldehyde of formula II with an amine of formula III yields the corresponding Schiff base having the formula

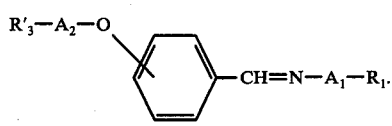

The reaction can be run in an organic solvent, e.g., an aromatic hydrocarbon such as toluene, and will preferably be run at the reflux temperature of the solvent.

Reduction of a compound of formula IV, using chemical or catalytic means, yields the corresponding intermediate having the formula

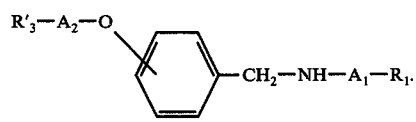

The reaction can be run using gaseous hydrogen in the presence of a catalyst such as Raney nickel of palladium. Preferably, the reaction will be run using a chemical reducing agent such as sodium borohydride.

The Schiff bases of formula IV and the compounds of formula V are novel compounds useful in the preparation of the antiinflammatory compounds of formula I; as such, they constitute a part of this invention.

The products of formula I, wherein $R_3$ is dialkylamino or a nitrogen containing heterocyclic group, can be prepared by reacting a compound of formula V, wherein $R'_3$ is dialkylamino or a nitrogen containing heterocyclic group, with an acid or sulfonyl halide, preferably an acid or sulfonyl chloride having the formula $$R_2-Cl, \quad \text{VI}$$

or when $R_2$ is

an acid anhydride having the formula

can also be used. The reaction can be run in an organic solvent, e.g., a halogenated hydrocarbon such as chloroform.

The products of formula I, wherein R₃ is alkylamino, can be prepared by first reacting a compound of formula V, wherein R'₃ is alkylbenzylamino, with a compound of formula VI or VII as described above to yield an intermediate having the formula

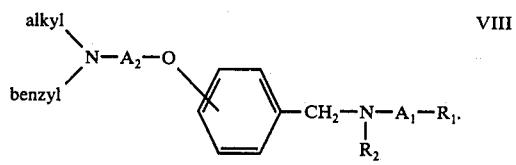

Debenzylation of a compound of formula VIII using the well-known catalytic hydrogenation procedure yields the corresponding product of formula I.

Those products of formula I wherein the R₁ or R₂ group contains an amino substituent are preferably prepared by reduction of the corresponding nitro compound.

The pharmaceutically acceptable salts of the compounds of formula I are readily prepared using procedures well known in the art. Acid addition salts are specifically contemplated. Exemplary salts are the hydrohalides, sulfate, nitrate, phosphate, oxalate, tartrate, maleate, citrate, benzenesulfonate, and others.

The compounds of formula I, and the pharmaceutically acceptable salts thereof, can be used for the treatment of inflammation in mammalian species such as mice, dogs, cats, monkeys, etc. Joint tenderness and stiffness (in conditions such as rheumatoid arthritis) are relieved by the compounds of this invention. Formulation of the compounds can be carried out according to accepted pharmaceutical practice in oral dosage forms such as tablets, capsules, elixirs or powders, or in injectable form in a sterile vehicle. The compounds of this invention can be administered in amounts of about 0.1 to 2.0 grams per 70 kilograms of animal body weight per day, preferably about 0.1 to 1.0 gram per 70 kilograms of animal body weight per day.

The following examples are specific embodiments of this invention.

EXAMPLE 1

N-[[2-[3-(Dimethylamino)propoxy]phenyl]methyl]-3-phenyl-N-(2-phenylethyl)-2-propenamide, oxalate salt (1:1)

(A)

N-[[2-[3-(Dimethylamino)propoxy]phenyl]methylene]-benzeneethanamine

A solution of 32.5 g of 2-(3-dimethylaminopropoxy)-benzaldehyde and 18.9 g of phenethylamine in 150 ml of toluene is heated at reflux for 1 hour. After 30 minutes, 1 mole equivalent of water is collected in a Dean-Stark trap. After cooling to approximately 50° C, the solvent is removed using a rotary evaporator and the oily residue is distilled to give 36.2 g of the title compound, boiling point 165°–167° C at 0.05 mm of Hg.

(B)

N-[[2-[3-(Dimethylamino)propoxy]phenyl]methyl]benzeneethanamine

A stirred solution of 36.0 g of N-[[2-[3-(dimethylamino)propoxy]phenyl]methylene]benzeneethanamine in 200 ml of methanol is treated portionwise with 13.0 g of sodium borohydride. The temperature is maintained at 35° C using a cold water bath. After 3 hours, the solvent is evaporated and the semi-solid residue is treated with 300 ml of water. The product is extracted twice with 100 ml portions of ether. The solvent fractions are combined, treated with water, dried and concentrated to give 33.8 g of an oily product. Distillation yields 19.9 g of the title compound, boiling point 165°–170° C at 0.15 mm of Hg.

(C)

N-[[2-[3-(Dimethylamino)propoxy]phenyl]methyl]-3-phenyl-N-(2-phenylethyl)-2-propenamide, oxalate salt (1:1)

A stirred solution of 4.30 g of cinnamoyl chloride in 35 ml of chloroform is cooled to 15° C and treated dropwise with a solution of 8.0 g of N-[[2-[3-(dimethylamino) propoxy]-phenyl]methyl]benzeneethanamine in 30 ml of chloroform. The temperature is maintained between 30 and 35° C using a cold water bath. After stirring at room temperature for 1 hour, the solution is heated at reflux for an additional hour, then cooled and concentrated to a semi-solid residue. An attempt to granulate this material is unsuccessful.

A solution of the semi-solid residue in 50 ml of water is treated with an excess of potassium carbonate. The base is extracted into ether, dried, and concentrated to give 10.6 g of an oily residue.

A solution of 8.0 g of oily residue in 25 ml of acetonitrile is treated with a solution of 1.6 g of oxalic acid in 20 ml of acetonitrile. The resulting solution is evaporated to a semi-solid residue. Trituration with a small amount of acetone gives 8.6 g of a colorless solid, melting point 74°–76° C.

EXAMPLE 2

N-[[4-[3-(Dimethylamino)propoxy]phenyl]methyl]-3-phenyl-N-(2-phenylethyl)-2-propenamide, oxalate salt (1:1)

A.

N-[[4-[3-(Dimethylamino)propoxy]phenyl]methylene]-benzeneethanamine 4-(3-Dimethylaminopropoxy)benzaldehyde (30.0 g) is reacted with 18 g of phenethylamine in 150 ml of toluene as described under Example 1 to give 41 g of an oil; boiling point 184°–189° C/0.1–0.2 mm of Hg.

B.

N-[[4-[3-(Dimethylamino)propoxy]phenyl]methyl]benzeneethanamine

Twenty grams of the Schiff base from part A is reduced with 7.2 g of sodium borohydride in 120 ml of methanol as described under Example 1 to give 15 g of product; boiling point 196°–200° C/0.2 mm of Hg.

C. N-[[4-[3-dimethylamino) propoxy]phenyl]methyl]-3-phenyl-N-(2-phenylethyl)-2-propenamide, oxalate salt (1:1)

The amine from part B (7.5 g) is reacted with 4.0 g of cinnamoyl chloride in 70 ml of chloroform as described under Example 1 (addition carried out at 10°–15° C). Since the syrupy residue from the chloroform evaporation cannot be crystallized, it is converted to the syrupy free base (potassium carbonate; ether extractions); weight, 8.9 g. The free base (8.6 g) and 1.8 g of oxalic acid are dissolved in 200 ml of warm acetonitrile, filtered, and the solvent removed on a rotary evaporator. The semi-solid residue is triturated with 50 ml of acetone and cooled overnight to give 8.6 g of solid; melting point 116°–118° C. Following crystallization from 45 ml of acetonitrile, the product weighs 6.8 g, melting point 116°–118° C.

EXAMPLE 3
N-Butyl-N-[[2-[3-(Dimethylamino)propoxy]phenyl]methyl]-3-phenyl-2-propenamide, maleate salt (1:1)

A.
N-[[2-[3-(Dimethylamino)propoxy]phenyl]methylene]-butanamine 2-(3-Dimethylaminopropoxy)benzaldehyde (32.5 g) is reacted with 11.5 g of n-butylamine in 150 ml of toluene as described in Example 1 to give 37.9 of oily product; boiling point 124°–128° C/0.1–0.2 mm of Hg.

B.
N-[[2-[3-(Dimethylamino)propoxy]phenyl]methyl]-butanamine

Nineteen grams of the material from part A is reduced with 8.2 g of sodium borohydride in 120 ml of methanol as described under Example 1 to give 16.4 of product; boiling point 145°–148° C/0.2 mm of Hg.

C.
N-Butyl-N-[[2-[3-(Dimethylamino)propoxy]phenyl]methyl]-3-phenyl-2-propenamide, maleate salt (1:1)

The amine from part B (8.0 g) is reacted with 5.3 g of 97% cinnamoyl chloride in 80 ml of chloroform as described under Example 1; the temperature is kept at 10°–15° C during the addition. Since the syrupy residue from the chloroform evaporation can not be crystalized it is converted to the oily free base (potassium carbonate; ether extractions); weight, 11.5 g. The latter (10.7 g) and 3.2 g of maleic acid are dissolved in 40 ml of acetonitrile, diluted to 250 ml with ether, seeded, and rubbed; the crystalline maleate salt gradually separates. After cooling for 3 days, the material is filtered under nitrogen, washed with ether, and dried in vacuo; weight, 11.2 g; melting point 82°–84° C (sintering at 78° C). Following crystallization from 40 ml of methanol-300 ml of ether, the product weighs 7.8 g, melting point 83°–85° C.

EXAMPLE 4
N-[[2-[3-(Dimethylamino)propoxy]phenyl]methyl]-N,3-diphenyl-2-propenamide, hydrochloride (1:1)

A.
N,N-Dimethyl-3-[2-[phenylimino)methyl]phenoxy]-propanamine

A solution of 32.5 g (0.156 mole) of 2-(3-dimethylaminopropoxy)benzalehye and 14.6 g (0.157 mole) of aniline in 150 ml of toluene is refluxed for 9 hours. Water which is formed very slowly is collected in a Dean-Stark trap. The bulk of solvent is removed on a rotary evaporator and the oily residue is fractionated to give 20.0 g of product; boiling point 165°–170° C/0.2 mm of Hg.

B.
2-[3-(Dimethylamino)propoxy]-N-phenylbenzenemethanamine

Ten grams of the material from part A is reduced with 4.0 g of sodium borohydride in 60 ml of methanol as described under Example 1 to give 7.8 g of product; boiling point 177°–182° C/0.1–0.2 mm of Hg. The viscous oil solidifies on rubbing; melting point 67°–69° C.

C.
N-[[2-[3-(dimethylamino)propoxy]phenyl]methyl]-N,3-diphenyl-2-propenamide, hydrochloride (1:1)

The amine from part B (7.7 g) is reacted with 4.7 g of 97% cinnamoyl chloride in 70 ml of chloroform as described under Example 1; the temperature is kept at 10°–15° C during the addition. The foamy residue from the chloroform evaporation is dissolved in 50 ml of acetonitrile and diluted to 200 ml with ether. On seeding and rubbing the crystalline hydrochloride salt slowly separates. After cooling overnight, the material is filtered under nitrogen, washed with ether, and dried in vacuo; weight, 11.5 g; melting point 152°–154° C. Recrystallization from 25 ml of acetonitrile yields 10.0g of product, melting point 154°–156° C.

EXAMPLE 5
N-[[2-[3-(Dimethylamino)propoxy]phenyl]methyl]-3-phenyl-N-(phenylmethyl)-2-propenamide, barbiturate salt (1:2)

A.
N,N-Dimethyl-3-[2-[[(phenylmethyl)imino]methyl]-phenoxy]propanamine

A solution of 20.0 g of 2-(3-dimethylaminopropoxy)-benzaldehyde and 10.3 g of benzylamine in 100 ml of toluene is heated at reflux for 1 hour in a procedure described for Example 1. The yield of product is 22.1 g, boiling point 175°–178° C/0.05 mm of Hg.

B.
2-[3-(Dimethylamino)propoxy]-N-(phenylmethyl)benzenemethanamine

A stirred solution of 18.0 g of amine from part A in 100 ml of methanol is treated portionwise with 6.8 g of sodium borohydride in a procedure described for Example 1. The yield of product is 12.8 g, boiling point 165°–168° C/0.2 mm of Hg.

C.
N-[[2-[3-(dimethylamino)propoxy]phenyl]methyl]-3-phenyl-N-(phenylmethyl)-2-propenamide, barbiturate salt (1:2)

A stirred solution of 4.9 g of cinnamoyl chloride in 35 ml of chloroform is cooled to 15° C and treated dropwise with a solution of 8.8 g of amine from part B according to a procedure for Example 1.

The crude product (semi-solid) is dissolved in 50 ml of water and treated with an excess of potassium carbonate. The base is extracted into ether, dried, and evaporated to give 12.4 g of an oily residue.

A solution of 11.2 g of the residue in 50 ml of methanol is treated with 3.3 g of barbituric acid. The resulting solution is evaporated to give an oil which gradually solidifies to yield 10.3 g of a solid, melting 170°–172° C, sintering at 164° C. Crystallization from 20 ml of dimethylformamide yields 5.2 g of solid, melting point 175°–177° C.

EXAMPLE 6
4-Chloro-N-[[2-[3-(dimethylamino)propoxy]phenyl]-methyl]-N-(2-phenylethyl)benzamide, oxalate salt (1:1)

Ten grams of N-[[2-[3-(dimethylamino)propoxy]-phenyl]-methyl]benzeneethanamine (see Example 1, part B) and 5.7 g of p-chlorobenzoyl chloride are reacted in 160 ml of chloroform as described under Example 1 (addition carried out at 10°–15° C). The glass-like residue from chloroform evaporation cannot be crystallized and is converted to the free base (potassium carbonate; ether extractions). The base (13.8 g) and 2.8 g of oxalic acid are dissolved in 40 ml of warm isopropanol. No crystallization occurs on cooling and rubbing, but on diluting with 400 ml of ether the oxalate salt is precipitated as a tacky solid which becomes completely granular when rubbed. After standing in the cold for about 16 hours, the material is filtered under nitrogen, washed with ether, and dried in vacuo; weight, 14.5 g; melting point 75°–77° C (foaming); sintering at 70° C. Crystallization from 30 ml of methanol-300 ml ether gives 14.0 g of colorless solid, melting point 78°–80° C (foaming); sintering at 70° C.

EXAMPLE 7

N-[[2-[3-(Dimethylamino)propoxy]phenyl]methyl]-N-(2-phenylethyl)benzamide, oxalate salt (1:1)

A solution of 5.0 g of N-[[2-[3-(dimethylamino)propoxy]phenyl]methyl]benzeneethanamine (prepared as described in Example 1) in 40 ml of chloroform is added dropwise to a stirred solution of 2.2 g of benzoyl chloride in 40 ml of chloroform. After completion of the addition, the solution is stirred at room temperature for 2 hours, heated at reflux for 1 hour, cooled and concentrated to give a viscous oily material.

An aqueous solution (25 ml) of the above is treated with an excess of potassium carbonate and the base is extracted into ether, dried, and concentrated to yield 6.3 g of oily material. The oxalic acid salt of this material is semi-solid and cannot be granulated.

A solution of 5.9 g of the above base in 25 ml of warm methanol containing 1.8 g of barbituric acid is concentrated to give an oil which gradually solidifies. Trituration with ether yields 7.0 g of solid, melting 178°–180° C. Crystallization from 30 ml of dimethylformamide gives 6.0 g of crystals, melting point 178°–180° C.

The above crystals are suspended in 50 ml of water and treated with 2 ml of 10% sodium hydroxide. The base is extracted into chloroform, dried, and concentrated to give 3.8 g of an oil. A solution of this material in 20 ml of acetonitrile containing 0.8 g of oxalic acid is concentrated to give a viscous oil. Trituration three times with ether gives 3.4 of a solid, melting point 60°–65° C. Crystallization from 6 ml of isopropanol yields 2.5 g of the title compound, melting point 65°–68° C.

EXAMPLE 8

N-[[2-[3-(Dimethylamino)propoxy]phenyl]methyl]-N-(2-phenylethyl)acetamide, oxalate salt (1:1)

A suspension of 9.0 g of N-[[2-[3-(dimethylamino)propoxy]phenyl]methyl]benzeneethanamine (prepared as described in Example 1) in 45 ml of acetic anhydride and 2 ml of pyridine is stirred and heated at reflux for one hour. The solution is cooled and most of the excess anhydride is evaporated to give an oily residue. This material is dissolved in 50 ml of water and treated with an excess of potassium carbonate. The base is extracted into 50 ml of ether, dried, and the solvent evaporated to give 9.6 g of oily material.

A solution of the above in 20 ml of acetonitrile is treated with a solution of 2.4 g of oxalic acid in 20 ml of acetonitrile. Seeding and cooling of this solution yields 11.0 g of material, melting point 120–122° C, sintering 110° C. Crystallization from 40 ml of acetonitrile gives 9.8 g of colorless solid, melting point 120°–122° C.

EXAMPLE 9

N-[[2-[3-(Dimethylamino)propoxy]phenyl]methyl]-N-(2-phenylethyl)methanesulfonamide, hydrochloride (1:1)

A stirred solution of 10 g of N-[[2-[3-(dimethylamino)propoxy]phenyl]methyl]benzeneethanamine in 50 ml of chloroform is treated dropwise at 10° to 15° C with 2.7 ml of methanesulfonyl chloride dissolved in 50 ml of chloroform, stirred for 1 hour at room temperature (some solid separates), refluxed for 1 hour (solution obtained), and maintained at room temperature for about 16 hours.

Evaporation of the chloroform yields 15 g of a solid; melting poing 175°–180° C (sintering at 135° C). The solid is crystallized from 200 ml of acetonitrile to give 10.5 g of material; melting point 196°–198° C (sintering at 193° C). Since microanalysis gives a high Cl value (probably due to the presence of a small quantity of the dihydrochloride salt of the starting diamine), the product is ground under 20 ml of water, kept 20 minutes, filtered, washed with some cold water and with ether, and air-dried; weight, 9.3 g; melting point 199°–201° C.

EXAMPLE 10

N-[[3-[3-(Methylamino)propoxy]phenyl]methyl]-3-phenyl-N-(2-phenylethyl)-2-propenamide, oxalate salt (1:1)

A.

N-[[3-[3-(N-benzyl-N-methylamino)propoxy]phenyl]methyl]-3-phenyl-N-(2-phenylethyl)-2-propenamide, oxalate salt (1:1)

Following the procedure of Example 1, but substituting 3-[3-(N-benzyl-N-methylamino)propoxy]benzaldehyde for 2-(3-dimethylaminopropoxy)benzaldehyde, yields the title compound.

B.

N-[[3-[3-(Methylamino)propoxy]phenyl]methyl]-3-phenyl-N-(2-phenylethyl)-2-propenamide, oxalate salt (1:1)

A suspension of 10 parts of material from part A in 100 ml of ethanol is treated with 1 part of 5% palladium on carbon and placed under 3 atmospheres of gaseous hydrogen and shaken until one equivalent of hydrogen is consumed. The mixture is filtered to remove the catalyst and the solvent evaporated under reduced pressure to yield the title compound.

EXAMPLE 11

N-[[2-[3-(Dimethylamino)propoxy]phenyl]methyl]-N-[2-(4-nitrophenyl)ethyl]-3-phenyl-2-propenamide, oxalate salt (1:1)

Following the procedure of Example 1, but substituting 4-nitrophenylethylamine for the phenethylamine, yields the title compound.

EXAMPLE 12

N-[2-(4-Aminophenyl)ethyl]-N-[[2-[3-(dimethylamino)propoxyl]-phenyl]methyl]-3-phenyl-2-propenamide, oxalate salt (1:1)

A suspension of 10 parts of N-[[2-[3(-dimethylamino)propoxy]phenyl]methyl]-N-[2-(4-nitrophenyl)ethyl]-3-phenyl-2-propenamide, oxalate salt (1:1) in 100 ml of ethanol is treated with 1 part of 5% palladium on carbon and placed under 3 atmospheres of gaseous hydrogen. The mixture is shaken until one equivalent of hydrogen is consumed, filtered and the solvent evaporated under reduced pressure to give the title compound.

EXAMPLES 13-30

Following the procedure (without the final salt formation) of Example 1, but substituting the compound listed in column I for 2-(3-dimethylaminopropoxy)benzaldehyde, the compound listed in column II for phenethylamine, and the compound listed in column III for cinnamoyl chloride, yields the compound listed in column IV.

EXAMPLE 31

4-Chloro-N-[[2-[3-(4-morpholinyl)propoxy]phenyl]methyl]-N-(2-phenylethyl)benzamide, methanesulfonate salt (1:1)

A. 2-[3-(4-Morpholinyl)propoxy]benzaldehyde

Salicylaldehyde (17g) is treated first with 6.7g of 50% sodium hydride in 110 ml of dimethylformamide and then with 92 ml of a 2N toluene solution of N-(3-chloropropyl)-morpholine. The mixture is heated at 105°–110° C for 4 hours, cooled and poured into 300 ml of water. The product is extracted three times with ether. The extracts are combined, dried, concentrated on a rotary evaporator and the residue distilled to give 32.3g of product as an oil, boiling point 155°–160° C at 0.1–0.2 mm of Hg.

|    | Column I | Column II | Column III | Column IV |
|----|----------|-----------|------------|-----------|
| 13 | 2-(2-diisopropylaminoethoxy)-benzaldehyde | n-butylamine | phenylacetyl chloride | N-butyl-N-[[2-]2-(diisopropylamino)ethoxy]phenyl]methyl]phenylacetamide |
| 14 | 2-[4-(1-pyrrolidinyl)butoxy]-benzaldehyde | n-pentylamine | propionyl chloride | N-pentyl-N-[[2-[4-(1-pyrrolidinyl)butoxy]phenyl]methyl]propionamide |
| 15 | 3-[2-(1-piperidinyl)ethoxy]-benzaldehyde | isopropylamine | benzoyl chloride | N-isopropyl-N-[[3-[2-(1-piperidinyl)ethoxy]phenyl]methyl]benzamide |
| 16 | 2-[5-(4-morpholinyl)pentoxy]-benzaldehyde | 4-chlorophenethylamine | benzoyl chloride | N-[[2-[5-(4-morpholinyl)pentoxy]phenyl]methyl]-N-[2-(4-chlorophenyl)ethyl]-benzamide |
| 17 | 4-[2-(1-piperazinyl)ethoxy]-benzaldehyde | 2-methoxyphenethylamine | benzoyl chloride | N-[[4-[2-(1-piperazinyl)-ethoxy]phenyl]methyl]-N-[2-(2-methoxyphenyl)ethyl]-benzamide |
| 18 | 2-[3-(4-methyl-1-piperazinyl)-propoxy]benzaldehyde | 3-trifluoromethylphenethylamine | benzoyl chloride | N-[[2-[3-(4-methyl-1-piperazinyl)propoxy]phenyl]methyl]-N-[2-(3-trifluoromethylphenyl)ethyl]benzamide |
| 19 | 2-(2-dimethylaminoethoxy)-benzaldehyde | 2-methylphenethylamine | cinnamoyl chloride | N-[[2-(2-dimethylamino)ethoxy]phenyl]methyl]-N-[2-(2-methylphenyl)-ethyl]-3-phenyl-2-propenamide |
| 20 | 2-(3-dimethylaminopropoxy)-benzaldehyde | cyclopropylamine | 3-(4-chlorophenyl)-2-propenoyl chloride | N-cyclopropyl-3-(4-chlorophenyl)-N-[[2-[3-(dimethylamino)propoxy]phenyl]-methyl]-2-propenamide |
| 21 | 2-(2-dimethylaminoethoxy)-benzaldehyde | cyclohexylamine | 3-(2-methylphenyl)-2-propenoyl chloride | N-cyclohexyl-N-[[3-[2-(dimethylamino)ethoxy]phenyl]methyl]-3-(2-methylphenyl)-2-propenamide |
| 22 | 2-(dimethylaminopropoxy)-benzaldehyde | cycloheptylamine | 3-(2-methoxyphenyl)-2-propanoyl chloride | N-cycloheptyl-N-[[2-[3-dimethylamino)propoxy]-phenyl]methyl]-3-(2-methoxyphenyl)-2-propenamide |
| 23 | 2-(3-dimethylaminopropoxy)-benzaldehyde | benzylamine | 4-bromobenzoyl chloride | N-benzyl-4-bromo-N-[[2-[3-(dimethylamino)propoxy]-phenyl]methyl]benzamide |
| 24 | 2-(3-dimethylaminopropoxy)-benzaldehyde | 2-methylbenzylamine | benzenesulfonyl chloride | N-[[2-[3-(dimethylamino)-propoxy]phenyl]methyl]-N-(2-methylbenzyl)benzenesulfonamide |
| 25 | 2-[4-(1-pyrrolidinyl)butoxy]-benzaldehyde | 3-trifluoromethyl-benzylamine | p-toluenesulfonyl-chloride | 4-methyl-N-[[2-[4-(1-pyrrolidinyl)butoxy]-phenyl]methyl]-N-(3-trifluoromethylbenzyl)-benzenesulfonamide |
| 26 | 3-[2-(1-piperidinyl)ethoxy]-benzaldehyde | 2-ethoxybenzylamine | 4-chlorobenzenesulfonyl chloride | 4-chloro-N-(2-ethoxybenzyl)-N-[[3-[2-(1-piperidinyl)-ethoxy]phenyl]methyl]benzenesulfonamide |
| 27 | 2-[3-(4-morpholinyl)propoxy]-benzaldehyde | 4-nitrobenzylamine | 4-nitrobenzenesulfonyl chloride | N-[[2-[3-(4-morpholinyl)-propoxy]phenyl]methyl]-N-(4-nitrobenzyl)-4-nitrobenzenesulfonamide |
| 28 | 2-(3-dimethylaminopropoxy)-benzaldehyde | t-butylamine | cyclohexanoyl chloride | N-(t-butyl)-N-[[2-[3-(dimethylamino)propoxy]phenyl]methyl]-cyclohexanamide |
| 29 | 2-(4-dimethylaminobutoxy)-benzaldehyde | p-toluidine | cycloheptanoyl chloride | N-[[2-[4-(dimethylamino)butoxy]-phenyl]methyl]-N-(4-(methylphenyl)-cycloheptanamide |
| 30 | 2-(2-methylethylaminoethoxy)-benzaldehyde | cyclopropylmethylamine | cinnamoyl chloride | N-cyclopropylmethyl-N-[[2-[2-(methylethylamino)ethoxy]phenyl]-methyl]-3-phenyl-2-propenamide |

B.
N-[[2-[3-(4-Morpholinyl)propoxy]phenyl]methylene]-benzeneethanamine

2-[3-(4-Morpholinyl)propoxy]benzaldehyde (31.7g) is reacted with 15.8g of phenethylamine in 130 ml of toluene following the procedure described in Example 1A to yield 34.3g of product as an oil, boiling point 215°–219° C at 0.2–0.3 mm of Hg.

C.
N-[[2-[3-(4-Morpholinyl)propoxy]phenyl]methyl]-benzeneethanamine

N-[[2-[3-(4-Morpholinyl)propoxy]phenyl]methylene]-benzeneethanamine (17g) is reduced with 5.4g of sodium borohydride in 85 ml of methanol following the procedure described in Example 1B to yield 12.8g of product as an oil, boiling point 219°–223° C at 0.1–0.2 mm of Hg.

D.
4-Chloro-N-[[2-[3-(4-morpholinyl)propoxy]phenyl]methyl]-N-(2-phenylethyl)benzamide, methanesulfonate salt (1:1)

N-[[2-[3-(4-Morpholinyl)propoxy]phenyl]methyl]-benzeneethanamine (12.7g) and 6.5g of p-chlorobenzoyl chloride are reacted in 180 ml of chloroform following the procedure described in Example 1C. The glass-like residue from the chloroform evaporation is rubbed under ether and the evaporation repeated to give 19.3g of a foamy residue. The residue is taken up in 70 ml of acetonitrile and diluted to 400 ml with ether. On seeding and rubbing, 16.8g of the crystalline hydrochloride salt separates, melting point 156°–158° C (sintering at 145° C). Following recrystallization from 60 ml of warm methanol-500 ml ether, the solid weighs 15.4g, melting point 156°–158° C (sintering at 147° C).

The hydrochloride salt is only slightly soluble in water. A portion of it is converted to the more soluble mesylate salt. Eight grams of the hydrochloride salt yields 7.4g of the oily base. The base and 1.5g of methanesulfonic acid are dissolved in 45 ml of acetonitrile and diluted to 225 ml with ether. On seeding and rubbing the title compound separates, yielding (after about 16 hours cooling) 8.1g of product, melting point 171°–173° C (sintering at 125° C). Recrystallization from 25 ml of warm acetonitrile-75 ml ether yields 7.7g of product, melting point 173°–175° C (sintering at 128° C).

EXAMPLE 32
N-[[2-[3-(4-Morpholinyl)propoxy]phenyl]methyl]-3-phenyl]N-(2-phenylethyl)-2-propenamide, hydrochloride (1:1)

N-[[2-[3-(4-Morpholinyl)propoxy]phenyl]methyl]-benzeneethanamine (19 g, see Example 31C) and 9.0 g of cinnamoyl chloride are reacted in 260 ml of chloroform as described in Example 9. The residue from the chloroform evaporation (after rubbing under ether and repeating the evaporation) is dissolved in 100 ml of acetonitrile, diluted to 400 ml with ether and maintained at a reduced temperature; the crystalline hydrochloride salt slowly separates. After 4 days at reduced temperature, the material is filtered, washed with ether and dried in vacuo to yield 22.7g of material, melting point 112°–114° C (sintering at 105° C). Following crystallization from 60 ml of warm acetonitrile-240 ml ether, the product weighs 21.5 g and has a melting point of 142°–144° C.

EXAMPLE 33
4-Chloro-N-[[2-[2-(4-morpholinyl)ethoxy]phenyl]methyl]-N-(2-phenylethyl)benzamide, hydrochloride salt (1:1)

A. 2-[2-(4-Morpholinyl)ethoxy]benzaldehyde

Salicylaldehyde (34 g) is treated first with 13.4 g of 50% sodium hydride in 220 ml of dimethylformamide and then with 185 ml of a 2N toluene solution of N-(2-chloroethyl)morpholine. The mixture is heated at 105°–110° C for 4 hours, cooled and poured into 300 ml of water. The product is extracted three times with ether. The extracts are combined, dried, concentrated on a rotary evaporator and the residue distilled to give 56.6 g of product as an oil, boiling point 145°–150° C at 0.05–0.1 mm of Hg.

B.
N-[[2-[2-(4-Morpholinyl)ethoxy]phenyl]methylene]-benzeneethanamine

2-[2-(4-Morpholinyl)ethoxy]benzaldehyde (55.9 g) is reacted with 29 g of phenethylamine in 240 ml of toluene following the procedure described in Example 1A to yield 68.8 g of product as an oil, boiling point 204°–210° C at 0.1–0.2 mm of Hg.

C.
N-[[2-[2-(4Morpholinyl)ethoxy]phenyl]methyl]benzeneethanamine

N-[[2-[2-(4-Morpholinyl)ethoxy]phenyl]methylene]-benzeneethanamine (68.5 g) is reduced with 22.5 g of sodium borohydride in 350 ml of methanol following the procedure described in Example 1B to yield 54 g of product as an oil, boiling point 216°–220° C at 0.2–0.3 mm of Hg.

D.
4-Chloro-N-[[2-[2-(4-morpholinyl)ethoxy]phenyl]methyl]-N-(2-phenylethyl)benzamide, monohydrochloride, hemihydrate N-[[2-[2-(4-Morpholinyl)ethoxy]phenyl]methyl]benzeneethanamine (40 g) and 22 g of p-chlorobenzoyl chloride are reacted in 600 ml of chloroform following the procedure described in Example 1C. The residue from the chloroform evaporation is first triturated with ether (evaporation repeated) and then with 400 ml of warm acetone to give a crystalline product. After diluting with 500 ml of ether and cooling for about 16 hours, the solid is filtered under nitrogen, washed with ether and dried in vacuo to yield 54.7 g of material, melting point 147°–149° C (sintering at 145° C). Crystallization from 250 ml of warm methanol-1750 ml ether yield 52.9 g of the title compound, melting point 147°–149° C.

EXAMPLE 34
4-Chloro-N-[[2-[3-(4-morpholinyl)propoxy]phenyl]methyl]-N-(2-phenylethyl)benzenesulfonamide, hydrochloride (1:1)

N-[[2-[3-(4-Morpholinyl)propoxy]phenyl]methyl]-benzeneethanamine (14g, see Example 31C) is reacted with 9.2 g of p-chlorobenzenesulfonyl chloride in 130 ml of chloroform. A solution of the amine in chloroform is added dropwise at 10°–15° C to a stirred solution of the p-chlorobenzenesulfonyl chloride in chloroform.

After the addition, the solution is stirred for 1 hour at room temperature and maintained for about 1 hour at room temperature. The chloroform is evaporated, and the residue is rubbed under ether. The resulting solid is taken up in acetonitrile, diluted with ether, rubbed and stored at a reduced temperature for several days, yielding 21.2 g of material, melting point 156°–158° C. Recrystallization from 130 ml of isopropanol yields 17 g of the title compound, melting point 163°–165° C.

EXAMPLE 35

4-Chloro-N-(2-phenylethyl)-N-[[2-[3-(1-piperidinyl)-propoxy]phenyl]methyl]benzamide, methanesulfonate salt (1:1)

(A) 2-[3-(1-Piperidinyl)propoxy]benzaldehyde

Salicylaldehyde (27g) is treated first with 11g of 50% sodium hydride in 175ml of dimethylformamide and then with 150ml of a 2N toluene solution of N-(3-chloropropyl)piperidine following the procedure described in Example 31A, yielding 47.7g of the title compound as an oil, boiling point 155°–160° C at 0.2–0.3mm of Hg.

(B)
N-[[2-[3-(1-Piperidinyl)propoxy]phenyl]methylene]-benzeneethanamine

2-[3-(1-Piperidinyl)propoxy]benzaldehyde (47.6g) is reacted with 24g of phenethylamine in 190ml of toluene following the procedure described in Example 1A to yield 61.9g of product as an oil, boiling point 214°–218° C. at 0.2–0.3mm of Hg.

(C)
N-[[2-[3-(1-Piperidinyl)propoxy]phenyl]methyl]benzeneethanamine

N-[[2-[3-(1-Piperidinyl)propoxy]phenyl]methylene]-benzeneethanamine (61.5g) is reduced with 20g of sodium borohydride in 320ml of methanol following the procedure described in Example 1B to yield 49.6g of product as an oil, boiling point 216°–221° C at 0.3–0.4mm of Hg.

(D)
4-Chloro-N-(2-phenylethyl)-N-[[2-[3-(1-piperidinyl-propoxy]phenyl]methyl]benzamide, methanesulfonate salt (1:1)

N-[[2-[3-(1-piperidinyl)propoxy]phenyl]methyl]-benzeneethanamine (25g)and 12.8g of p-chlorobenzoyl chloride are reacted in 360ml of chloroform following the procedure described in Example 1C (addition at 10°–15° C). The residue from the chloroform evaporation crystallized when rubbed under ether (evaporation repeated) and triturated with 100ml of warm acetonitrile yielding 33.4g of hydrochloride salt (after cooling for about 16 hours), melting point 161°–163° C.

The hydrochloride salt is less than 1% soluble in water, so it is converted to the more soluble methenesulfonate salt. Thirty-three grams of the hydrochloride salt yield 31.5g of the viscous oily base. The base and 6.5g of methanesulfonic acid are dissolved in 170ml of acetonitrile and diluted to 1.5 liter with ether. On seeding and rubbing the title compound separates, yielding (after 4 days in the cold) 30.2g of product, melting point 102°–104° C. Recrystallization from 90ml of warm acetonitrile-500ml ether yields 28.4g of product, melting point 102°–104° C.

What is claimed is:

1. A compound having the formula

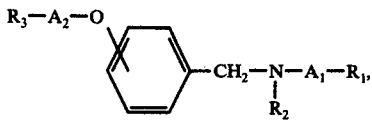

or a pharmaceutically acceptable salt thereof, wherein $R_1$ is alkyl, cycloalkyl or aryl; $R_2$ is

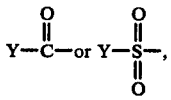

wherein Y is styryl or styryl substituted in the phenyl ring with a halogen, alkyl, alkoxy, trifluoromethyl, nitro or amino group; $R_3$ ia 1-pyrrolidinyl, 1-piperidinyl, 4-morpholinyl, 1-piperazinyl, or 4-alkyl-1-piperazinyl; $A_1$ is a saturated bond or an alkylene group having 1 to 4 carbon atoms; and $A_2$ is an alkylene group having 2 to 5 carbon atoms; and wherein aryl is phenyl or phenyl substituted with a halogen, alkyl, alkoxy, trifluoromethyl, nitro, or amino group; alkyl and alkoxy are groups having 1 to 6 carbon atoms; and cycloalkyl is a group having 3 to 7 carbon atoms.

2. A compound in accordance with claim 1 having the formula

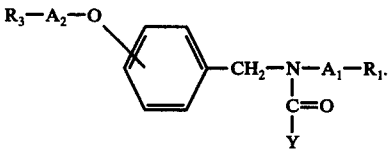

3. A compound in accordance with claim 1 having the formula

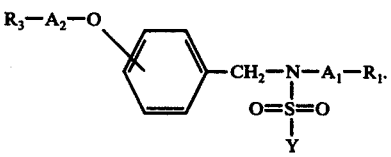

4. A compound in accordance with claim 1 wherein $R_1$ is alkyl.

5. A compound in accordance with claim 1 wherein $R_1$ is aryl.

6. A compound in accordance with claim 2 wherein $R_3$ is 4-morpholinyl.

7. A compound in accordance with claim 3 wherein $R_3$ is 4-morpholinyl.

8. A compound in accordance with claim 6 wherein $A_2$ is —(CH$_2$)$_2$— or —(CH$_2$)$_3$—.

9. The compound in accordance with claim 6 having the name N-[[2-[3-(4-morpholinyl)propoxy]phenyl]methyl]-3-phenyl-N-(2-phenylethyl)-2-propenamide, hydrochloride (1:1).

* * * * *

UNITED STATES PATENT AND TRADEMARK OFFICE
CERTIFICATE OF CORRECTION

PATENT NO. : 4,122,255
DATED : October 24, 1978
INVENTOR(S) : John Krapcho

It is certified that error appears in the above-identified patent and that said Letters Patent are hereby corrected as shown below:

Column 2, line 37, "nickel of" should read --nickel or--.

Column 5, line 53, "benzalehye" should read --benzaldehyde--.

Column 10, Example 13, Column IV "N-butyl-N-[[2]2-" should read --N-butyl-N-[[2-[2- --.

Column 9, Example 21, Column I, "2-" should read --3- --.

Column 9, Example 22, Column I, "2-dimethylaminopropoxy)-" should read --2-(3-dimethylaminopropoxy)- --.

Column 14, line 22, "ia" should read --is--.

Signed and Sealed this

Sixth Day of February 1979

[SEAL]

Attest:

RUTH C. MASON
Attesting Officer

DONALD W. BANNER
Commissioner of Patents and Trademarks